US011819252B2

(12) United States Patent
Babic et al.

(10) Patent No.: US 11,819,252 B2
(45) Date of Patent: Nov. 21, 2023

(54) SYSTEM FOR IMPLANTING IN BONE TISSUE

(71) Applicant: KONINKLIJKE PHILIPS N.V., Eindhoven (NL)

(72) Inventors: Drazenko Babic, Best (NL); Thirukumaran Thangaraj Kanagasabapathi, Eindhoven (NL); Susanne Maaike Valster, Valkenswaard (NL); Bernardus Hendrikus Wilhelmus Hendriks, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 284 days.

(21) Appl. No.: 17/234,882

(22) Filed: Apr. 20, 2021

(65) Prior Publication Data

US 2021/0236179 A1 Aug. 5, 2021

Related U.S. Application Data

(63) Continuation of application No. 15/763,645, filed as application No. PCT/EP2016/072336 on Sep. 21, 2016, now Pat. No. 10,993,748.

(30) Foreign Application Priority Data

Sep. 30, 2015 (EP) .................................. 15187681

(51) Int. Cl.
*A61B 17/70* (2006.01)
*A61B 17/86* (2006.01)
(Continued)

(52) U.S. Cl.
CPC .......... *A61B 17/7098* (2013.01); *A61B 17/68* (2013.01); *A61B 17/7032* (2013.01);
(Continued)

(58) Field of Classification Search
CPC ...... A61B 17/8805; A61B 2017/00026; A61B 2017/00061
(Continued)

(56) References Cited

U.S. PATENT DOCUMENTS

2004/0073221 A1* 4/2004 Biscup ................. A61N 1/205
606/301
2004/0260229 A1* 12/2004 Meir ...................... A61B 5/031
604/9

(Continued)

FOREIGN PATENT DOCUMENTS

WO 2006070961 A2 7/2006
WO 2008089429 A2 7/2008
(Continued)

OTHER PUBLICATIONS

Mobbs, R.J. et al "Technique, Challenges and Indications for Percutaneous Pedicle Screw Fixation", Journal of Clinical Neuroscience, vol. 18, 2011, pp. 741-749

Nachabe, R. et al "Estimation of Biological Chromophores using Diffuse Optical Spectroscopy: Benefit of Extending the UV-VIS Wavelength Range to include 1000 to 1600nm" Optical Express, vol. 18, 2010, pp. 879-888.

(Continued)

*Primary Examiner* — Eduardo C Robert
*Assistant Examiner* — Tara Rose E Carter (57) ABSTRACT

The invention relates a system for implanting an implantable device in bone tissue, a processing unit for such system, a method of implanting an implantable device and a method of providing information for an implanting of an implantable device. In view of the finding that a fat content in cancellous bone is higher than a fat content in compact bone, the lipids fraction, which can be determined by optical means, e.g. spectroscopy, can be used to determine correct screw placement in healthy bone.

20 Claims, 4 Drawing Sheets

(51) Int. Cl.
*A61B 17/88* (2006.01)
*A61B 17/68* (2006.01)
*A61B 17/00* (2006.01)

(52) U.S. Cl.
CPC ........ *A61B 17/864* (2013.01); *A61B 17/8805* (2013.01); *A61B 17/8875* (2013.01); *A61B 2017/00026* (2013.01); *A61B 2017/00057* (2013.01); *A61B 2017/00061* (2013.01); *A61B 2017/00128* (2013.01); *A61B 2017/883* (2013.01)

(58) Field of Classification Search
USPC ........................................ 606/250–279, 86 A
See application file for complete search history.

(56) References Cited

U.S. PATENT DOCUMENTS

| | | | |
|---|---|---|---|
| 2005/0143732 A1* | 6/2005 | Burch | A61N 5/0601 606/53 |
| 2006/0036259 A1* | 2/2006 | Carl | A61B 17/7064 606/90 |
| 2008/0228231 A1 | 9/2008 | Raphael | |
| 2009/0163901 A1* | 6/2009 | Fisher | A61B 17/7032 606/301 |
| 2011/0060240 A1 | 3/2011 | Londot | |
| 2011/0152790 A1 | 6/2011 | Dacey | |
| 2012/0232407 A1 | 9/2012 | Fisher | |

FOREIGN PATENT DOCUMENTS

| | | |
|---|---|---|
| WO | 2009111387 A1 | 9/2009 |
| WO | 2011054124 A1 | 5/2011 |
| WO | 102011017602 A1 | 10/2012 |

OTHER PUBLICATIONS

Nachabe, R. et al "Estimation of Lipid and Water Concentrations in Scattering Media with Diffuse Optical Spectroscopy from 900 to 1600 nm", Journal of Biomedical Optics, vol. 15, May 2010, pp. 037015-10.

Duck, F.A. Physical Properties of Tissue: A Comprehensive reference book, 1990 Academic Press.

Farrel, T.J. et al "A Diffusion Theory Model of Spatially Resolved, Steady-State Diffuse Reflectance for the Non-Invasive Determination of Tissue Optical Properties", Medical Physics, vol. 19, 1992, pp. 879-888.

Mueller, M. et al "Recovering Intrinsic Fluorescence by Monte Carlo Modeling", Journal Biomedical Optics, vol. 18, 2013, pp. 027009-1 to 027009-13.

Gabriel, C. et al "Compilation of Dielectric Properties of Body Tissues at RF and Microwave Frequencies", Radiofrequency Radiation Standards NATO ASI Series, vol. 274, 1995, pp. 187-196.

Yablonovitch, E. "Photonic Crystals: Semiconductors of Light", Scientific American ISSN: 0036-8733, vol. 285, No. 6, 2001, pp. 46-55.

Schaefer, C.G. et al "Reversible Light, Thermo, and Mechano-Responsive Elastomeric Polymer Opal Films", Chemistry of Materials, vol. 25, 2013, pp. 2309-2318.

Pursiainen, O.L.J. et al "Nanoparticle-Tuned Structural Color from Polymer Opals", Optics Express, ISSN: 1094-4087 vol. 15, 2007, p. 9553.

Seeboth, A. et al "Piezochromic Polymer Materials Displaying Pressure Changes in Bar-Ranges" American Journal of Materials Science 2011.

Sagara, Y. et al, "Mechanically induced Luminescence Changes in Molecular assemblies", Nature Chemistry vol. 1, 2009, pp. 605-610.

Teng, M.J. et al "Reversible Tuning Luminescent Color and Emission Intensity: A Dipeptide-based Light-Emitting Material" Advanced Materials, vol. 24, pp. 1255-1261, 2012.

\* cited by examiner

SYSTEM FOR IMPLANTING IN BONE TISSUE

CROSS-REFERENCE TO PRIOR APPLICATIONS

This is a Continuation of application Ser. No. 15/763,645, filed on Mar. 27, 2018, which is the the U.S. National Phase application under 35 U.S.C. § 371 of International Application No. PCT/EP2016/072336, filed on Sep. 21, 2016, which claims the benefit of European Patent Application No. 15187681.0, filed on Sep. 30, 2015. These applications are hereby incorporated by reference herein.

FIELD OF THE INVENTION

The present invention relates to a system for implanting an implantable device in bone tissue, the implantable device having an internal chamber for receiving an optical transmission device, a processing unit for such system for implanting an implantable device in bone tissue, a method of assisting in implanting an implantable device, a method of providing information for an implanting of an implantable device and a software product for providing information for an implanting of an implantable device.

BACKGROUND OF THE INVENTION

In a number of medical procedures and contexts, an implantable device is at temporarily implanted in bone tissue, e.g. for fixing the bone tissue in relation to other bone tissue or for fixing the bone tissue in relation of an external surrounding.

Examples of such clinical applications include pedicle screw insertions in the cervical, thoracic and lumbar spine, fracture fixations in various bone traumas, and plate positioning in hip and knee arthroplasties.

Pedicle screw fixations (see, for example, R. J. Mobbs, P. Sivabalan and J. Li, "Technique, challenges and indications for percutaneous pedicle screw fixation", Journal of Clinical Neuroscience 18 (2011), pp. 741-749) are a mainstay in treatment of spinal degenerative disease, intervertebral disc disease, spinal traumas or spinal deformities. Pedicle screw fixation provides short, rigid segmental stabilization that allows preservation of motion segments and stabilization of the spine. Fusion rates and clinical outcome in the treatment of thoracolumbar fractures appear to be superior to that achieved using other forms of treatment. According to a report by the Agency for Healthcare Research and Quality (AHRQ), approximately 488,000 spinal fusions were performed during U.S. hospital stays in 2011 (a rate of 15.7 stays per 10,000 population), which accounted for 3.1% of all operating room procedures.

The safety and the effectiveness of pedicle-screw instrumentation in the spine have been questioned despite its use worldwide to enhance stabilization of the spine. There are two major concerns related to the pedicle screw placement:

1. Accurate positioning of the pedicle screws—pedicle screws are inserted either blindly or under often-poor fluoroscopic guidance. Lately some navigation technologies are employed, with limited clinical outcomes so far.
2. Pedicle screw loosening—often time pedicle screws are placed in elderly with spine degenerative problems where osteoporosis is a common condition. Screw loosening happens in approximately one third of patients within two years after the surgical treatment.

SUMMARY OF THE INVENTION

It is an object of the present invention to provide for improvements in the implantation of implantable devices in bone tissue, in particular in terms of accuracy and reliability. In particular, as an example of such implantable device, it is desirable to provide an accurate placement of pedicle screws in human spine with a capability of surrounding tissue sensing while inserting the screw. Getting close to vital structures (spinal cord, spinal nerves) or being misplaced laterally (muscular bundles) may be timely detected and prevented. It is further aimed at providing a detection system that allows measuring the hardness of the bone during placement in order to judge whether additional measures should be taken to secure the screw.

In a first aspect of the present invention a system for implanting an implantable device in bone tissue is presented, the implantable device having an internal chamber for receiving an optical transmission device, the system comprising, a light detector configured to be coupled to the optical transmission device at least when the latter has been received in the internal chamber of the implantable device so as to receive the light reflected by and/or scattered in tissue adjacent the implantable device and detect at least a part of the spectrum thereof, a calculation unit for calculating a parameter indicative for a fat content in the tissue from the detected spectrum, and a navigation unit for comparing the calculated parameter indicative for the fat content with a predetermined value and outputting a signal indicative of a result of the comparing.

For example, the optical transmission device may comprise at least one optical waveguide arranged for transmitting light from a proximal end of the optical transmission device to a distal end to illuminate tissue and for transmitting light reflected by and/or scattered in the tissue from the distal end of the optical transmission device to the proximal end. Thereby, when the optical waveguide has been received in the internal chamber of the implantable device, an optical connection is established between a front portion of the device and a distal end of the waveguide, which is preferably connectable to the light detector. Thus, the light detector may receive light reflected by and/or scattered in tissue in front of the implantable device, as seen in a movement direction of the device during an implantation. From the detected light and in particular its spectrum, a parameter indicative for a fat content of tissue in front of the device may be determined.

Also, in a second aspect of the invention, a processing unit for a system for implanting an implantable device in bone tissue is provided, comprising a calculation unit for calculating a parameter indicative for a fat content in the tissue from a detected spectrum of light reflected by and/or scattered in the tissue, and a navigation unit for comparing the calculated parameter indicative for the fat content with a predetermined value and outputting a signal indicative of a result of the comparing.

In a third aspect of the invention, a method of assisting in implanting an implantable device is provided, comprising the steps of providing an optical waveguide in an internal chamber of the implantable device, the optical waveguide being arranged for transmitting light from a proximal end of the optical transmission device to a distal end to illuminate tissue and for transmitting light reflected by and/or scattered in the tissue from the distal end of the optical transmission device to the proximal end, transmitting light from a proximal end of the optical transmission device to a distal end to illuminate tissue, transmitting light reflected by and/or scattered in the tissue from the distal end of the optical transmission device to the proximal end, receiving the light reflected by and/or scattered in the tissue and detecting at least a part of the spectrum thereof, calculating a parameter indicative for a fat content in the tissue from the detected spectrum, comparing the calculated parameter indicative for the fat content with a predetermined value, and outputting a signal indicative of a result of the comparing.

In a further, forth, aspect of the invention, a method of providing information for an implanting of an implantable device is provided, comprising the steps of detecting at least a part of the spectrum of light reflected by and/or scattered in the tissue, calculating a parameter indicative for a fat content in the tissue from the detected spectrum, comparing the calculated parameter indicative for the fat content with a predetermined value, and outputting a signal indicative of a result of the comparing.

It was found by the inventor that the fat content in cancellous bone (i.e. inner, soft (or softer) portion of a bone) is higher than the fat content in compact bone (i.e. outer and hard (or harder) portion of the bone). In other words, the lipids fraction, which can be determined by optical means, e.g. spectroscopy, can be used to determine correct screw placement in healthy bone. It was found when determining a parameter that is related to the lipid fraction in bone that when the lipid fraction is above a certain value that the implantable device is still in cancellous bone. When the value drops below the cutoff value the compact bone is reached and further advancing the implantable device might damage to the surrounding soft tissues of the bone.

In a preferred embodiment, the navigation unit is arranged for outputting a warning to a user of the system indicating that the hard shell portion of the bone is reached if the result of the comparing indicates that the calculated parameter indicative for the fat content is less than the predetermined value.

In a preferred embodiment, the system further comprises a determining unit arranged for setting the predetermined value, based on a spectrum detected at a position of the implantable device for which the bone tissue type is known.

It is to be noted that the predetermined value may be determined separately for each patient, even though it is also contemplated that a standardized predetermined value may be provided, e.g. selected for a set of values depending on certain parameters of the patient. It is also possible to provide that the predetermined value reflects rather a relative value in relation of a value present in a known inner portion of the bone.

One option for detecting a transition from cancellous bone (soft bone) to compact bone (hard bone) is based on the fat content dropping below a predefined and absolute value. Another option, which might also be combined with the above option, includes determining the fat content (or a parameter indicative thereof) when the implantable device (e.g. the combination of optical stylet/screw) is in cancellous bone (i.e. the fat content is relatively high). When advancing the implantable device the fat content will drop when the front portion of the device (specifically the device tip i.e. the viewpoint of the optical transmission device arranged therein) is approaching the compact bone.

In an exemplary embodiment, when the fat content (or parameter indicative thereof) of tissue adjacent the front portion of the device drops by more than 20% compared to that of the value in cancellous bone, the tip of the implantable device is considered as being close to the compact bone and a warning signal to the physician is be given. In a more preferred embodiment the drop is more than 40%. In an even more preferred embodiment the drop is more than 50%.

In a preferred embodiment, the system further comprises a probe arrangement for measuring an electrical impedance of tissue adjacent to the implantable device, and an operating unit for operating the probe arrangement, wherein the navigation unit is further arranged to determine a characteristic of the tissue and/or a type of the tissue from the operation of the operation unit.

As a further means for obtaining information about the surrounding tissue, the electrical impedance can be measured by a suitable probe arrangement.

In a preferred embodiment, the implantable device is a pedicle screw and the system further comprises a screwing tool arranged for being coupled to the pedicle screw for turning the pedicle screw, wherein the screwing tool includes a recess or channel in which the optical waveguide is received.

Further preferably, the optical waveguide or the optical transmission device is arranged for being fixed to the implantable device in such manner that an axial movement (i.e. a movement in and out of the implantable device along its longitudinal axis or direction of insertion into the tissue) is prevented while a relative rotational movement between the optical transmission device or the optical waveguide and the implantable device is allowed. That is, the implantable device may rotate freely about the optical waveguide. Accordingly, the optical transmission device or the optical waveguide do not have to follow the rotational aspect of the screwing motion involved with implanting, such that the optical transmission device or the optical waveguide do not become twisted.

In a preferred embodiment, the system further comprises a light source configured to be coupled to the optical waveguide for illuminating the tissue through the optical waveguide.

In a preferred embodiment, the system further comprises a fluid dispensing unit configured to be coupled with the implantable device, wherein the fluid dispensing unit is arranged for dispensing a liquid through the implantable device into the tissue.

The fluid to be dispensed may be, for example, a biocompatible cement, which may be used for further securing the implantable device inside the bone and/or for strengthening the bone tissue surrounding the implantable device.

In a preferred embodiment, the system further comprises a pressure sensitive portion provided at the distal end of the optical transmission device in optical connection with the optical waveguide, the pressure sensitive portion forming part of an outer surface of the implantable device, wherein the pressure sensitive portion exhibits an optical response indicative of an amount of pressure applied to the pressure sensitive portion, wherein the light detector is arranged for detecting the optical response, wherein the system further comprises a pressure determination unit for a calculating a pressure applied to the pressure sensitive portion and outputting a signal indicative of said pressure.

By means of the pressure sensitive portion, information about a pressure at or around the implantable device can be derived, which can be used for obtaining information about the bone itself, about the positioning of the implantable device (e.g. the pressure depends on characteristics of the surrounding tissue) and also about a curing of an implanted liquid (like a biocompatible cement).

In a modification of the above embodiment, the system further comprises the implantable device and the pressure sensitive portion is a part of the implantable device and/or the optical transmission device is arranged such that, upon insertion of the optical transmission device into the implantable device, the pressure sensitive portion forms part of an outer surface of the implantable device.

The pressure sensitive portion may be provided as part of the implantable device and/or as part of the optical transmission device (which is then fixed in the implantable device).

In a further modification of the above embodiment, the pressure sensitive portion includes piezochromic and/or piezoluminescent material.

In case of a piezoluminescent material light is emitted by such material depending on the pressure, such that for determining the pressure it is not even necessary to provide a light source outside the implantable device.

In a further aspect of the present invention a computer program is presented for providing information for an implanting of an implantable device, the software product comprising program code means for causing a processing unit according to the invention to carry out the steps of the method for providing information according to the invention when the software product is run on the processing unit.

Independently from the navigation based on the parameter indicative for the fat content of the (bone) tissue, it is also contemplated as part of the invention and the present disclosure that a pressure sensitive portion is provided in the implantable device and/or the optical waveguide, allowing for a determination of the in-situ pressure.

In particular, an implantable apparatus is provided, arranged for being implanted in bone tissue, comprising an optical waveguide arranged for transmitting light from a distal end of the optical waveguide to a proximal end of the optical waveguide, an implantable device having an internal chamber in which the optical waveguide is received, and a pressure sensitive portion provided at an outer surface portion of the implantable device in contact with tissue upon implantation, wherein the pressure sensitive portion exhibits an optical response indicative of an amount of pressure applied to the pressure sensitive portion, wherein the pressure sensitive portion and the optical waveguide are arranged such that there is a line of sight between the pressure sensitive portion and the distal end of the optical waveguide.

Preferably, the pressure sensitive portion includes piezochromic and/or piezoluminescent material. With piezoluminescent material, i.e. material emitting light in case pressure is exerted, there is no need for illumination from the outside.

Preferably, the optical waveguide is removably received in the internal chamber.

Preferably, also in this context, the implantable device is a pedicle screw.

Preferably, the implantable device includes at least one channel for introducing a fluid into the tissue.

Preferably, the optical waveguide is arranged for transmitting light from the proximal end to the distal end for illuminating tissue and for transmitting light reflected from the tissue from the distal end to the proximal end.

Preferably, the implantable apparatus further comprises a probe arrangement for measuring an electrical impedance of tissue adjacent to the implantable device.

In addition, an implantable device is provided, arranged for being implanted in bone tissue, comprising an internal chamber arranged for receiving an optical transmission device, and a pressure sensitive portion provided at an outer surface portion of the implantable device in contact with tissue upon implantation, wherein the pressure sensitive portion exhibits an optical response indicative of an amount of pressure applied to the pressure sensitive portion, wherein the internal chamber and the pressure sensitive portion are arranged such that there is a line of sight for an optical transmission device received in the internal chamber to the pressure sensitive portion.

Furthermore, an optical transmission device is provided arranged for being received in an internal chamber of an implantable device, the implantable device for being implanted in bone tissue, the optical transmission device comprising an optical waveguide arranged for transmitting light from a distal end of the optical transmission device to a proximal end of the optical transmission device, and a pressure sensitive portion provided at the distal end of the optical transmission device in optical connection to the optical waveguide, wherein the pressure sensitive portion exhibits an optical response indicative of an amount of pressure applied to the pressure sensitive portion, wherein the optical transmission device is arranged such that, upon insertion of the optical transmission device into the implantable device, the pressure sensitive portion forms part of an outer surface of the implantable device.

Yet further, a system for implanting an implantable device in bone tissue is provided, comprising at least one of the implantable apparatus discussed above, the implantable device discussed above with an optical transmission device including an optical waveguide received in the internal chamber of the implantable device such that there is a line of sight for the optical transmission device to the pressure sensitive portion, and the optical transmission device discussed above received in an implantable device having an internal chamber in which the optical transmission device is received such that the pressure sensitive portion forms part of an outer surface of the implantable device, wherein the system further comprises an optical detector coupled to the optical waveguide for detecting the optical response of the pressure sensitive portion, and a processing unit coupled to the optical detector for calculating a pressure applied to the pressure sensitive portion and outputting a signal indicative of said pressure.

Preferably, the system comprises a light source coupled to the optical waveguide for illuminating the tissue through the optical waveguide. Here, it is particularly preferred that the optical detector is further arranged for detecting light reflected from illuminated tissue, wherein the processing unit is further arranged to determine a characteristic of the tissue and/or a type of the tissue from the reflected light detected by the optical detector.

Preferably, the system further comprises a probe arrangement for measuring an electrical impedance of tissue adjacent to the implantable device, and an operation unit for operating the probe arrangement, wherein the processing unit is further arranged to determine a characteristic of the tissue and/or a type of the tissue from the operation of the operation unit.

Preferably, the implantable device is a pedicle screw and the system further comprises a screwing tool arranged for being coupled to the pedicle screw for turning the pedicle screw, wherein the screwing tool includes a recess or channel in which the optical waveguide is received.

In addition, a method of assisting in implanting an implantable device is provided, comprising the steps of providing an optical waveguide in an internal chamber of the implantable device, the optical waveguide being arranged for transmitting light from a distal end of the optical transmission device to a proximal end of the optical transmission device, providing a pressure sensitive portion at the distal end of the optical waveguide or providing the distal end of the optical waveguide at the pressure sensitive portion, wherein the portion exhibits an optical response indicative of an amount of pressure applied to the pressure sensitive portion and the pressure sensitive portion forms part of an outer surface of the implantable device, wherein during an implanting of the implantable device the optical response of the pressure sensitive portion is detected and a pressure applied to the pressure sensitive portion is calculated based on the detected response.

It shall be understood that the system for implanting of claim 1, the processing unit of claim 11, the method of assisting in implanting of claim 12, the method of providing information of claim 13 and the computer program of claim 14 have similar and/or identical preferred embodiments, in particular, as defined in the dependent claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figures 1, 2:
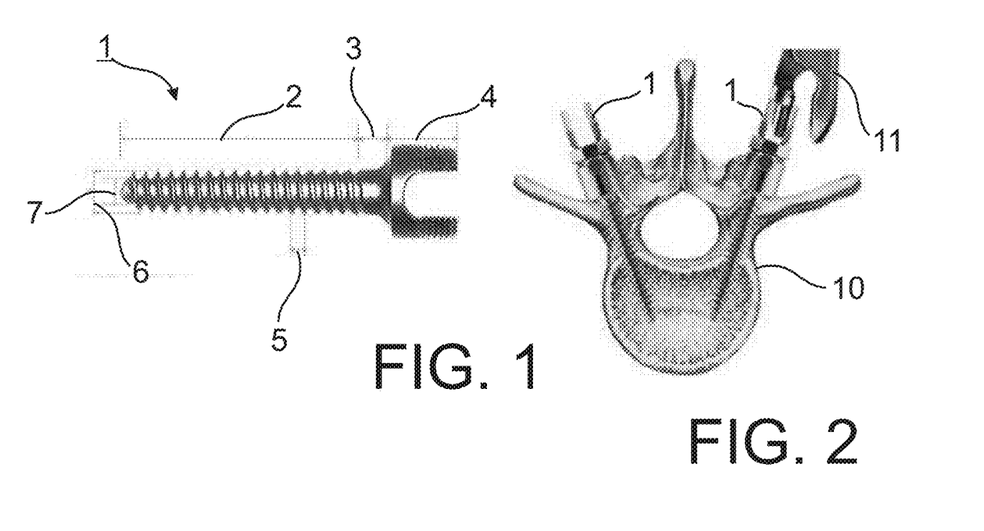
FIG. 1 shows a principle concept of a pedicle screw.
FIG. 2 shows two pedicle screws placed in a vertebra.

FIG. 1 shows a principle concept of a pedicle screw 1. The pedicle screw 1 includes a body 2, a neck 3 and a head 4. The body 2 is provided with a thread having a pitch 5, and outer diameter 6 and an inner diameter 7, such that the thread depth is the difference between the outer diameter 6 and the inner diameter 7.

FIG. 2 shows two pedicle screws 1 placed in a vertebra 10 together with a tool 11 for screwing the screw 1 into the bone.

As the skilled person is familiar with the general concepts of a pedicle screw as an example of an implantable device for being implanted into bone tissue and other such implantable devices for bone tissue, the tools already conventionally used in such context and the concepts of conventional placing the implantable devices into the bone tissue, further explanation thereof is not provided here.

Figure 3:
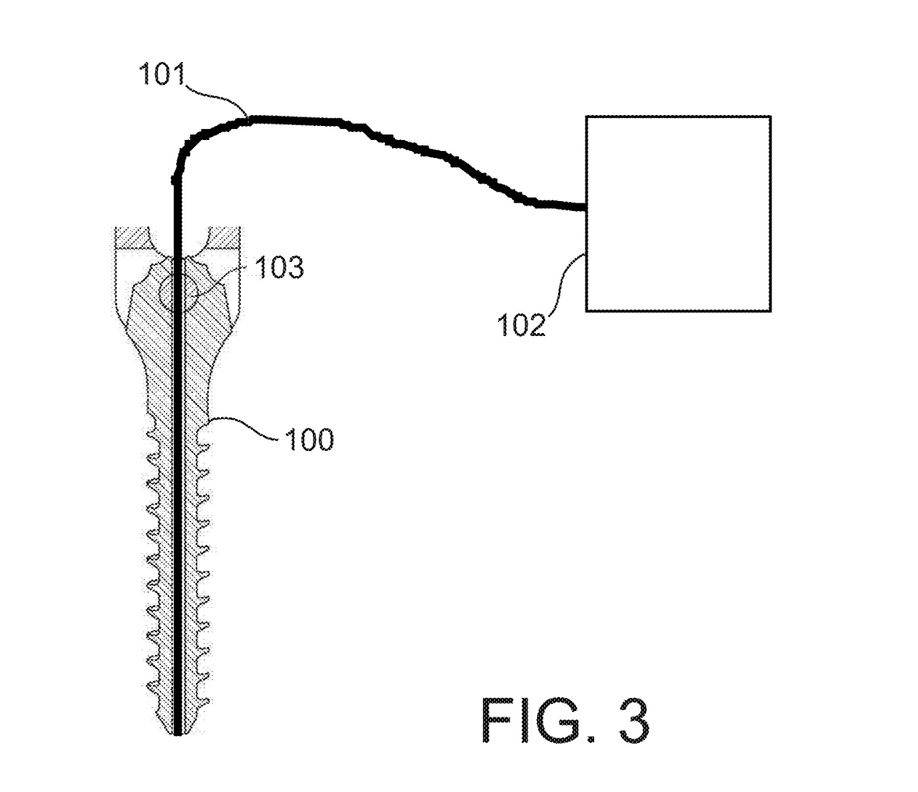
FIG. 3 shows a combination of a pedicle screw, an optical transmission device and a processing unit in accordance with an embodiment of the invention.

FIG. 3 shows a combination of a pedicle screw 100, an optical transmission device 101 and a processing unit 102 in accordance with an embodiment of the invention.

The pedicle screw 100 has a hollow shaft 103, into which an optical stylet 104 of the optical transmission device 101 is inserted such that the optical stylet 104 extends to the distal tip of the screw 100. The stylet 104 and the whole optical transmission device 101 contain a waveguide such as an optical fiber that is connected to a processing unit 102 (an optical console) that is capable of sending and receiving light. The received light is spectrally analyzed allowing tissue discrimination at the tip of the screw 100. For instance techniques like diffuse reflectance spectroscopy, fluorescence spectroscopy, RAMAN spectroscopy, OCT can be applied.

Specifically, the received light is used for a determination of the parameter indicative for the fat content of the (bone) tissue in front of the tip of the screw 100 and the optical stylet 101, which, in turn, is used for determining whether the bone tissue is that of the soft(er) part of the bone or that of the hard(er) part of the bone, thereby allowing for a navigation assistance in placing the screw 100.

Figure 4:
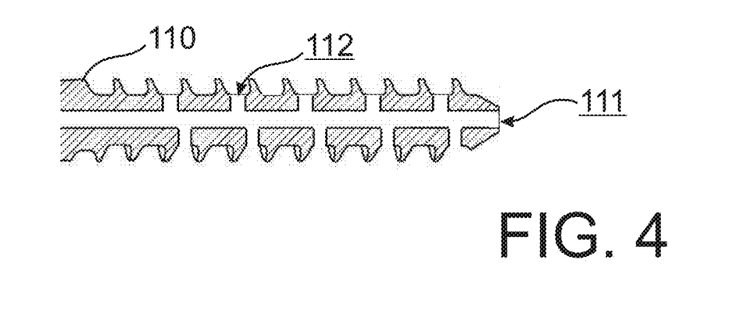
FIG. 4 shows a portion of a pedicle screw in accordance with another embodiment of the invention.

FIG. 4 shows a portion a pedicle screw 110 in accordance with another embodiment of the invention. As discussed already with respect to FIG. 3, the pedicle screw 110 includes a hollow shaft, such that there is an internal chamber 111 inside the pedicle screw 110 extending through the pedicle screw 110. Into such internal chamber 111, the optical transmission device or optical waveguide may be inserted (not shown here), such that optical measurements at the tip (or other parts) of the pedicle screw 110 can be performed. The pedicle screw 110 is further provided with openings 112 branching off from the internal chamber 111. The openings 112 allow, for example, for fluids to be injected through the pedicle screw 110 into the surrounding (bone) tissue (not shown).

In a further preferred embodiment (not shown), the internal chamber 111 may be provided with a notch for example adjacent its rear portion. In the notch, a fixating element such as a small screw may be provided. When a stylet 104 has been introduced into the internal chamber 111, the fixating element may be used to fixate the stylet in the axial direction. However, the fixation is such that a free rotational movement of the pedical screw 110 about the stylet 104 is still possible, thus avoiding twisting of the stylet 104 during implantation of the screw.

Figure 5:
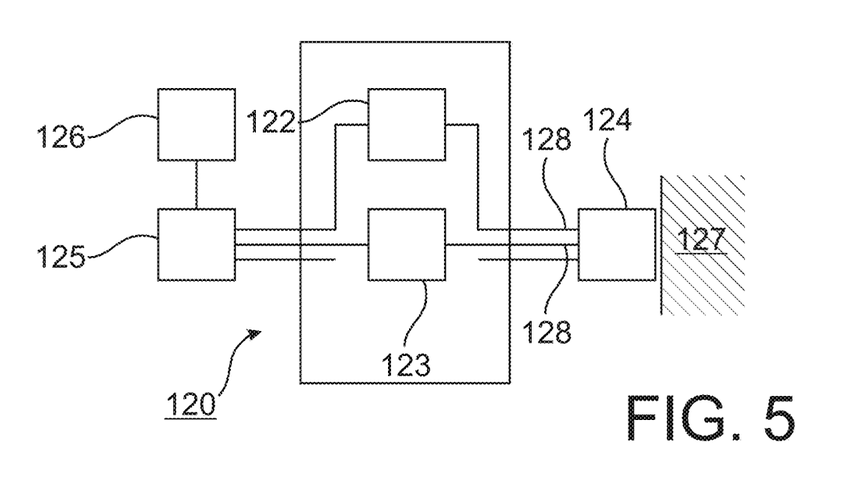
FIG. 5 shows a system for implanting an implantable device in accordance with another embodiment of the invention.

FIG. 5 shows a system 120 for implanting an implantable device (not shown) in accordance with another embodiment of the invention.

The probe 124 contains two light guides 128. These light guides 128 of the probe 124 are connected to an optical console 121. These light guides are understood to be for instance optical fibers or other optical waveguides. Specifically, in the present embodiment, the system comprises a light source 122 in the form of a halogen broadband light source with an embedded shutter, the probe 124 (or optical transmission device) which is to be inserted in the implantable device (not shown) and an optical detector 123. The optical detector 123 can resolve light with a wavelength substantially in the visible and infrared regions of the wavelength spectrum, such as from 400 nm to 1700 nm. The combination of light source 122 and detector 123 allows for diffuse reflectance (DRS) and fluorescence measurements of the tissue 127 in front of the distal end of the waveguides 128. For a detailed discussion on DRS measurements, incorporating reference is made to R. Nachabé, B. H. W. Hendriks, M. V. D. Voort, A. E, and H. J. C. M. Sterenborg, "Estimation of biological chromophores using diffuse optical spectroscopy: benefit of extending the UV-VIS wavelength range to include 1000 to 1600 nm," (Optics Express, vol. 18, 2010, pp. 879-888) and R. Nachabe, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm," (Journal of Biomedical Optics, vol. 15, May. 2010, pp. 037015-10). From these DRS measurements, tissue transitions can be deduced, wherein furthermore specifically a parameter indicative of a fat content of the tissue can be obtained.

Although diffuse reflectance spectroscopy is described above to extract tissue properties, other optical methods can also be envisioned like diffuse optical tomography by employing a plurality of optical fibers, differential path length spectroscopy, fluorescence and Raman spectroscopy. Additionally, acquisition of optical data could be done via a probe that is contact with the tissue or via a non-contact probe.

A processor 125, to which data storage 125 is connected, transforms the measured spectra in the detector 123 into physiological parameters that are indicative of the tissue state for the source-detector fiber combination. To determine whether a certain tissue is in front of the probe (or implantable device), the signal for the source-detector pair can be compared with a look-up-table. Another way is to translate the measured parameters into physiological parameters and define ranges for these parameters for each tissue type. Incorporating referral is made to Duck, F. A., "Physical properties of tissue: A comprehensive reference book" (1990, Academic Press, Harcourt Brace Jovanovich, Publishers), where methods based on classification and regression tree (CART) analyses are described for classifying tissue based on these physiological parameters.

Figure 9:
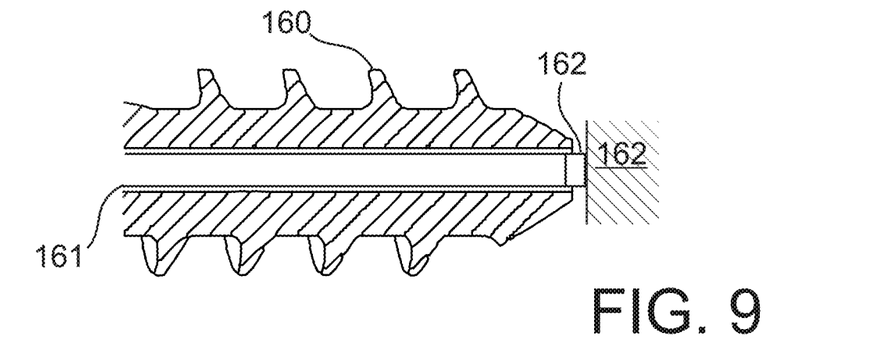
FIG. 9 shows a part of an arrangement including a pedicle screw, an optical transmission device with a pressure sensitive portion and adjacent tissue in accordance with another embodiment of the invention.

Apart from the tissue sensing, the illumination fiber 128 is partly covered by an on pressure color changing material (not shown, see FIG. 9). Part of the light in the illumination fiber 128 is reflected by this color changing material and received by the console 121. The reflected wavelength depends on the applied pressure. By measuring for instance the wavelength where the peak intensity of the reflected light is located, the pressure that was exercised on the on pressure changing material can now be deduced. In this way not only the tissue properties can be deduced but also the pressure that is exercised on the screw while being inserted can be determined. Apart from the optical spectroscopy measurements that provide information the tissue in front of the screw this pressure sensing material provide also information that can be used as additional confirmation. When the screw is in the softer interior of the bone the pressure found will be lower than that when the screw is near or in the boundary of the bone. Furthermore, the hardness of the bone marrow can be assessed. Based on the measured pressure the physician can decide whether or not additional measures must be taken, for instance injecting material via the ports of the screw that enforces the inside of the bone (see FIG. 4).

An example of extracting the physiological parameter is by fitting the acquired spectra using a custom made Matlab 7.9.0 (Mathworks, Natick, Mass.) algorithm. In this algorithm, a widely accepted analytical model was implemented, namely the model introduced by T. J. Farrel, M. S. Patterson and B. C. Wilson, "A diffusion theory model of spatially resolved, steady-state diffuse reflectance for the non-invasive determination of tissue optical properties," (Med. Phys. 19 (1992) p. 879-888), which is hereby incorporated by reference in entirety. The input arguments for the model of Farrel et al. are the absorption coefficient $\mu_a(\lambda)$, the reduced scattering coefficient $\mu_s'(\lambda)$ and the center-to-center distance between the emitting and collecting fibers at the tip of the probe. For a complete description of the diffusion theory model, referral is made to the paper of Farrel et al.

In the following, the model will be explained briefly. The formulas are mainly based on the work of Nachabé et al. mentioned above (R. Nachabé, B. H. W. Hendriks, M. V. D. Voort, A. E, and H. J. C. M. Sterenborg, "Estimation of biological chromophores using diffuse optical spectroscopy: benefit of extending the UV-VIS wavelength range to include 1000 to 1600 nm," (Optics Express, vol. 18, 2010, pp. 879-888)), which is hereby incorporated by reference in entirety, and furthermore reference is made in this context also to R. Nachabe, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm," (Journal of Biomedical Optics, vol. 15, May 2010, pp. 037015-10), which is hereby incorporated by reference in entirety.

A double power law function can be used to describe the wavelength dependence of the reduced scattering coefficient, where the wavelength $\lambda$ is expressed in nm and is normalized to a wavelength value of $\lambda_0=800$ nm. The parameter a corresponds to the reduced scattering amplitude at this specific wavelength.

$$\mu_s'(\lambda) = a\left(\rho_{MR}\left(\frac{\lambda}{\lambda_0}\right)^{-b} + (1-\rho_{MR})\left(\frac{\lambda}{\lambda_0}\right)^{-4}\right) [\text{cm}^{-1}] \quad \text{(Eq. 1)}$$

In this equation the reduced scattering coefficient is expressed as the sum of Mie and Rayleigh scattering where $\rho_{MR}$ is the Mie-to-total reduced scattering fraction. The reduced scattering slope of the Mie scattering is denoted as b and is related to the particle size.

Figure 6:
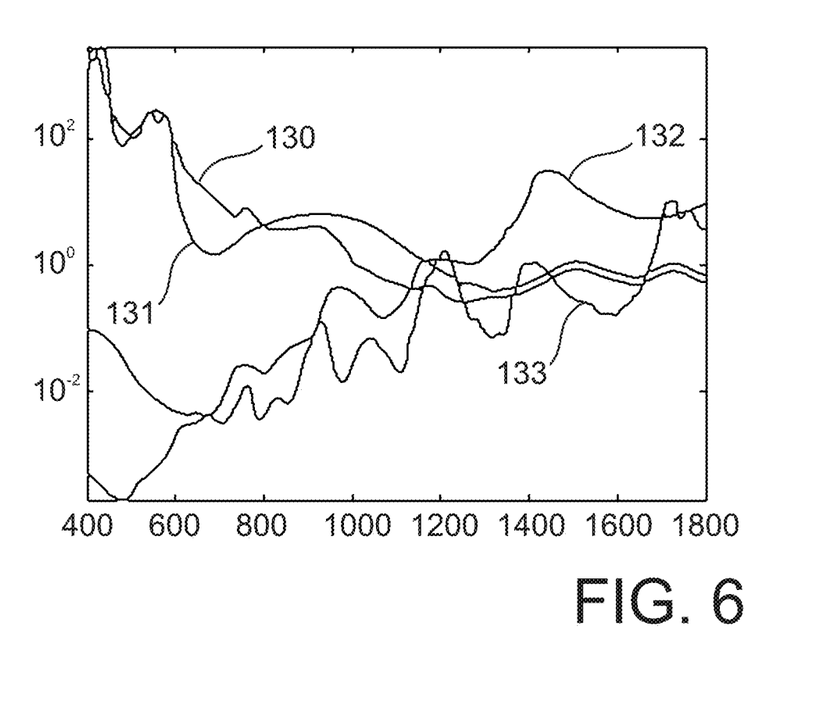
FIG. 6 shows a log plot of the absorption spectra of blood, water and fat.

For a homogeneous distribution of absorbers, the total light absorption coefficient $\mu_a(\lambda)$ can be computed as products of the extinction coefficients and volume fraction of the absorbers (see FIG. 6, which shows a log plot of the absorption spectra of blood (hemoglobin (line 130), oxygenated hemoglobin (line 131), water (line 132) and fat (line 133), with the abscissa indicating the wavelength in nm and the ordinate showing $\mu_a(\lambda)$ in $\text{cm}^{-1}$)):

$$\mu_a^{Total} = f_1\mu_a^1 + f_2\mu_a^2 + f_3\mu_a^3 + \ldots \quad \text{(Eq.2)}$$

Instead of modeling the absorption coefficient $\mu_a(\lambda)$ as the sum of absorption coefficients weighted by the respective concentrations of the four chromophores of interest, it was decided to express the tissue absorption coefficient as $$\mu_a^{Tissue}(\lambda) = C(\lambda)v_{Blood}\mu_a^{Blood}(\lambda) + v_{WL}\mu_a^{WL}(\lambda)[\text{cm}^{-1}] \quad \text{(Eq.3)}$$

where $\mu_a^{Blood}(\lambda)$ corresponds to the absorption by blood and $\mu_a^{WL}(\lambda)$ corresponds to absorption by water and lipid together in the probed volume. The volume fraction of water and lipid is $v_{WL}=[\text{Lipid}]+[\text{H}_2\text{O}]$, whereas $v_{Blood}$ represents the blood volume fraction for a concentration of hemoglobin in whole blood of 150 mg/ml.

The factor C is a wavelength dependent correction factor that accounts for the effect of pigment packaging and alters for the shape of the absorption spectrum. This effect can be explained by the fact that blood in tissue is confined to a very small fraction of the overall volume, namely blood vessels. Red blood cells near the center of the vessel therefore absorb less light than those at the periphery. Effectively, when distributed homogeneously within the tissue, fewer red blood cells would produce the same absorption as the actual number of red blood cells distributed in discrete vessels. The correction factor can be described as $$C(\lambda) = \frac{1 - \exp(-2R\,\mu_a^{Blood}(\lambda))}{2R\,\mu_a^{Blood}(\lambda)}, \quad (\text{Eq. 4})$$

where R denotes the average vessel radius expressed in cm. The absorption coefficient related to blood is given by $$\mu_a^{Blood}(\lambda) = \alpha_{BL}\mu_a^{HbO_2}(\lambda) + (1-\alpha_{BL})\mu_a^{Hb}(\lambda)[\text{cm}^{-1}], \quad (\text{Eq.5})$$

where $\mu_a^{HbO_2}(\lambda)$ and $\mu_a^{Hb}(\lambda)$ represent the basic extinction coefficient spectra of oxygenated hemoglobin HbO$_2$ and deoxygenated hemoglobin Hb, respectively. The oxygenated hemoglobin fraction in the total amount of hemoglobin is noted as $\alpha_{BL}$=[HbO$_2$]/([HbO$_2$]+[Hb]) and is commonly known as the blood oxygen saturation. The absorption due to the presence of water and lipid in the measured tissue is defined as $$\mu_a^{WL}(\lambda) = \alpha_{WL}\mu_a^{Lipid}(\lambda) + (1-\alpha_{WL})\mu_a^{H_2O}(\lambda)[\text{cm}^{-1}] \quad (\text{Eq.6})$$

In this case the concentration of lipid related to the total concentration of lipid and water together can be written as $\alpha_{WF}$=[Lipid]/([Lipid]+[H$_2$O]), where [Lipid] and [H$_2$O] correspond to the concentration of lipid (density of 0.86 g/ml) and water, respectively.

This way of relating the water and lipid parameters in the expression of the absorption coefficient is defined in Eq.6, rather than estimating separately the water and lipid volume fraction corresponding to a minimization of the covariance of the basic functions for fitting, thus resulting in a more stable fit (see, also for further explanation and validation of this theorem the above mentioned papers by R. Nachabé et al.).

Other optical absorbers could also be incorporated into this algorithm, such as: lycopene, vitamin A, β-carotene, bile, or black tar (or any absorbing substance related to smoking).

Another way to discriminate differences in spectra is by making use of a principal component analysis. This method allows classification of differences in spectra and thus allows discrimination between tissues. It is also possible to extract features from the spectra.

Figure 7:
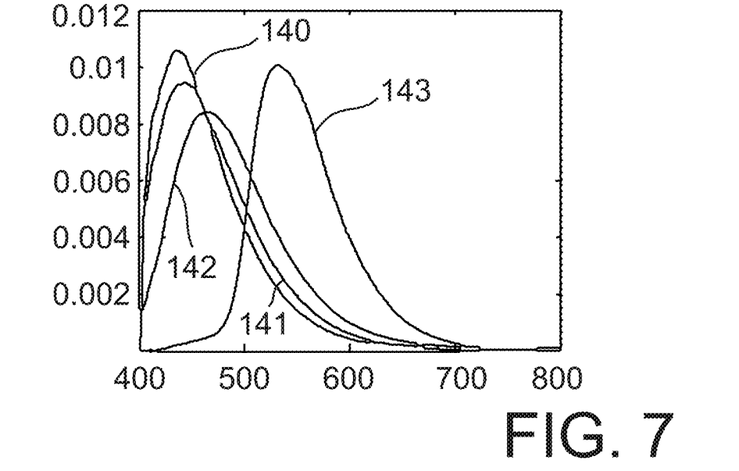
FIG. 7 shows intrinsic fluorescence curves for collagen, elastin, NADH and FAD.

Apart from diffuse reflectance one could also measure fluorescence spectra. Then for instance parameters like collagen, elastin, NADH and FAD could also be measured (see FIG. 7, which shows intrinsic fluorescence curves for collagen (line 140), elastin (line 141), NADH (line 142) and FAD (line 143), with the abscissa providing the wavelength in nm and the ordinate giving the fluorescence intensity in arbitrary units). The ratio NADH/FAD, which is called the optical redox parameter, is of interest because it is an indicator for the metabolic state of the tissue (see M. Müller and B. H. W. Hendriks, "Recovering intrinsic fluorescence by Monte Carlo modeling", (J. Biomed. Optics vol. 18 (2013) p. 027009-1 to 027009-13) and references therein), which can also be used to discriminate tissues.

Figure 8:
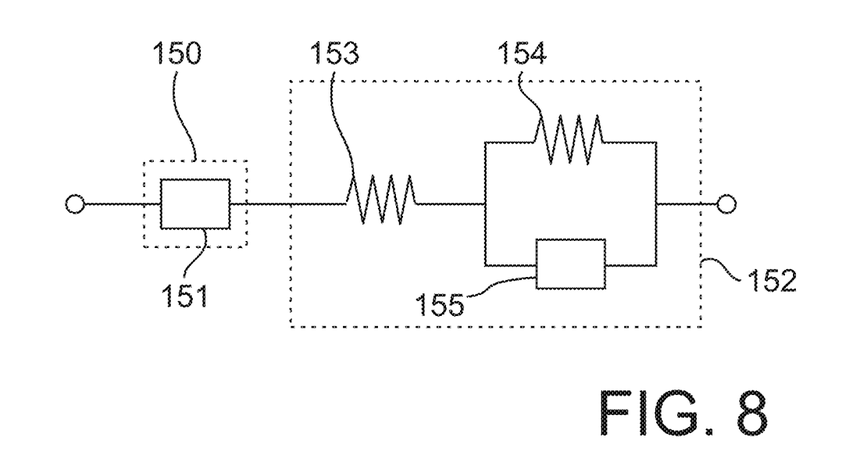
FIG. 8 shows a diagram illustrating an equivalent circuit for measuring tissue impedance.

FIG. 8 shows a diagram illustrating an equivalent circuit for measuring tissue impedance.

Dielectric properties (permittivity ε' and conductivity σ) of an unknown sample (e.g. pedicle, vertebral body, spinal nerve and spinal cord) can be calculated from measurements of the impedance of the probe against the unknown sample using the following relationships where so is the permittivity of free space $$\varepsilon' = \frac{C}{K}$$
$$\sigma = \frac{G\varepsilon_0}{K} \quad (\text{Eq. 7 + 8})$$

where C and G are the fringing capacitance and conductance of the probe. The characteristic parameters of the probe can be calculated from measurements of the impedance components of the probe in air and in a standard sample (water or salt solution).

In the case of biological samples, the dielectric properties of the materials are a measure of their interaction with electromagnetic fields and varies significantly based on the type of tissue (see the table below based on Duck, F. A., "Physical properties of tissue: A comprehensive reference book" (1990 Academic Press, Harcourt Brace Jovanovich, Publishers) and C. Gabriel, et al. "Compilation of dielectric properties of body tissues at RF and microwave frequencies" (Radiofrequency Radiation Standards NATO ASI Series Volume 274, 1995, pp 187-196)). Frequency dependent dielectric properties of the tissues can be measured using several impedance matching techniques i.e. Wien-bridge oscillators. A suitably calibrated probe can be used to measure the tissue impedance in frequency ranges from 10 Hz to 20 GHz. The phenomenon is equivalent to a frequency dependent capacitor in series with a resistor (see FIG. 8 showing an electrode component 150 with a constant phase element 151 in series with a tissue component including a resistance 153 in series with a parallel provision of a further resistance 154 and another constant phase element 155). Both components can be approximated by negative power functions of frequency i.e. their absolute values decrease with increasing frequency.

| Tissue Type | Tissue Conductivity (S/m) |
| --- | --- |
| Bone-Cancellous | 0.07 |
| Bone-Marrow | 0.05 |
| Cartilage | 0.18 |
| Cerebro Spinal Fluid | 2.0 |
| Fat | 0.04 |
| Muscle | 0.375 |
| Blood | 0.7 |
| Nerve | 0.03 |

FIG. 9 shows a part of an arrangement including a pedicle screw 160, an optical transmission device 161 with a pressure sensitive portion 162 and adjacent tissue 163 in accordance with another embodiment of the invention.

Due to the insertion or implanting of the pedicle screw 160, of which only the tip is shown, a pressure exists between the pressure sensitive portion 162 of the optical transmission device 161 (which is fixed against axial movement in the screw 160) and the adjacent tissue 163 (e.g. bone).

Pressure can be sensed with an optical signal using, for example, photonic crystals. Photonic crystals may be formed by a combination of at least 2 material types, where one has a high dielectric constant and the other has a low dielectric constant (for example air). The material has a periodic pattern in the refractive indices, with a typical length scale of 100-1000 nm allowing interaction with visible light, described by the Bragg reflection. Changing this periodical pattern, for example by pressure or stretch, will change this interaction, observable by a difference in the reflected wavelength (color). The material class is highly adjustable, so the range and sensitivity can be tuned towards the requirements of the application (see, for example, E. Yablonovitch, "Photonic Crystals: Semiconductors of Light" (Scientific American ISSN: 0036-8733 Vol: 285 (6) 2001 Page: 46-55); C. G. Schäfer, et al. "Reversible Light, Thermo., and Mechano-Responsive Elastomeric Polymer Opal Films" (Chemistry of Materials, 2013, 25, pp 2309-2318) and O. L. J. Pursiainen, et al. "Nanoparticle-tuned structural color from polymer opals" (Optics Express ISSN: 1094-4087, Vol: 15 2007, Page: 9553).

Examples of pressure sensitive photonic crystal materials include nanopores filled with air in a polymer matrix, for example poly(alkyl-methacrylate) matrix with monodisperse spherical nanopores in a highly ordered pattern, commercialized by the Canadian company Opalux and also nanospheres in a polymer matrix, for example hard cross-linked polystyrene (PS) spheres coated with a thin polymethyl-methacrylate (PMMA) inter-layer which anchors the outer shell composed of soft polyethylacrylate (PEA) (see, O. L. J. Pursiainen, et al. "Nanoparticle-tuned structural color from polymer opals" (Optics Express ISSN: 1094-4087, Vol: 15 2007, Page: 9553)).

Pressure induced color changing material can also be made of liquid crystals, for example developed by the Fraunhofer Institute (see, A. Seeboth, et al. "Piezochromic Polymer Materials Displaying Pressure Changes in Bar-Ranges" (American Journal of Materials Science 2011, volume 1, page 139-134). Currently, however, this material is not yet commercially available.

Furthermore optical pressure sensing can also be done by using dye-doped polymers (see, Y. Sagara, et al. "Mechanically induced luminescence changes in molecular assemblies" (Nature chemistry 2009, volume 1, page 605-610)) or light emitting materials (see, M-J. Teng, et al. "Reversible Tuning Luminescent Color and Emission Intensity: A Dipeptide-Based Light-Emitting Material" (Advanced materials 2012, volume 24, page 1255-1261).

In any case, the skilled person will appreciate that the pressure sensitive portion 162 may be provided by any suitable means, including piezochromic and piezoluminescent materials.

The use of pressure sensing in this way includes as advantages a high simplicity (no electronic components, no labor-intensive electronic assembly), therefore possible cost reduction; a possibility for further miniaturization (no limitation due to electrical cables or interconnects), mechanical flexibility and MR, EM and RF compatibility.

Figure 10:
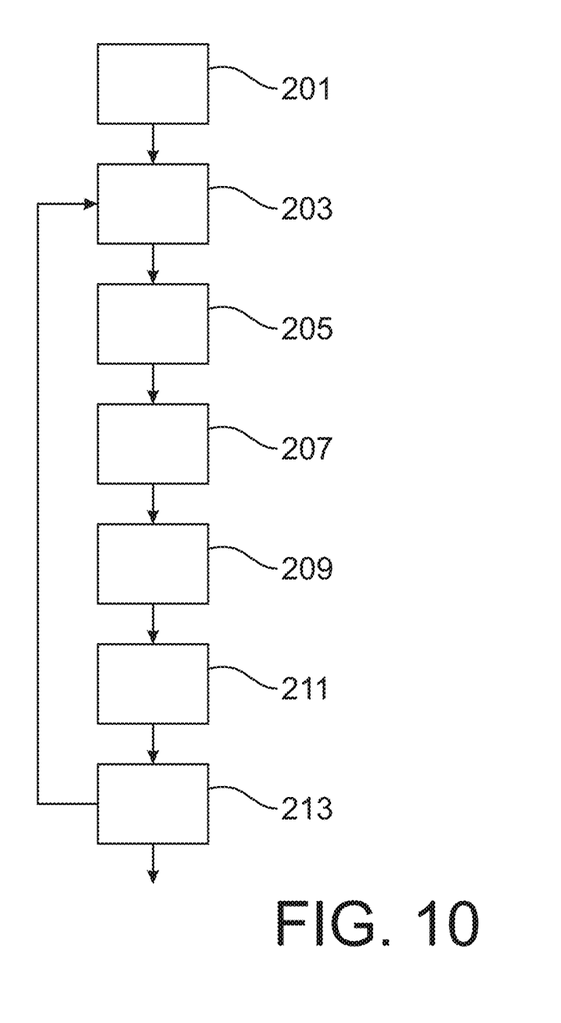
FIG. 10 shows a flow diagram illustrating a method of assisting in implanting an implantable device in accordance with an embodiment of the invention.

Furthermore, there is the possibility to integrate multi sensing modalities on the interventional device. This may lead to distributed sensing along the interventional devices shaft, sensing a variety of parameters with only one device, or a combination of both. FIG. 10 shows a flow diagram illustrating a method of assisting in implanting an implantable device in accordance with an embodiment of the invention.

In a preparation step 201, an optical waveguide is provided in an internal chamber of the implantable device, the optical waveguide being arranged for transmitting light from a proximal end of the optical transmission device to a distal end to illuminate tissue and for transmitting light reflected by and/or scattered in the tissue from the distal end of the optical transmission device to the proximal end.

During the actual implanting procedure, in an illuminating step 203 light is transmitted from a proximal end of the optical transmission device to a distal end to illuminate tissue.

In a reflecting step 205, light reflected by and/or scattered in the tissue is transmitted from the distal end of the optical transmission device to the proximal end. In a reception step 207, the light reflected by and/or scattered in the tissue is received and at least a part of the spectrum thereof is detected.

Based on the detected spectrum, in a calculation step 209, a parameter indicative for a fat content in the tissue is calculated.

In a comparison step 211, the calculated parameter indicative for the fat content is compared with a predetermined value and in an output step 213, a signal indicative of a result of the comparing is outputted.

During the procedure, a loop including steps 203 to 213 is repeated as long as needed.

After the insertion or implanting is provided, the optical transmission device may be removed from the implanted device.

In an embodiment of the present invention, at least one optical sensor is incorporated (inserted) into a pedicle screw capable of performing measurements near the screw. The sensor is in communication with a console that based on the sensed data is able to determine the tissue type near the screw. In this way, when the screw is advanced, the tissue sensing allows the physician to avoid misplacement of the screw.

In a preferred modification of the embodiment as the sensor an optical stylet is provided inside the center of the pedicle screw including of a waveguide capable of sending to and receiving light from the tip of the screw that based on optical spectroscopy allows tissue discrimination at the tip of the screw. This tissue information is provided to the physician during the screw placement due to which screw misplacement can be avoided.

A further aspect of the embodiment is that at least one of the distal ends of the fiber that is in contact with the tissue is covered by a pressure sensitive material that changes color upon application of pressure. The pressure load on the material at the tip results in a well-defined color change from which the pressure can be deduced. The color change is detected by the optical console used to perform the optical spectroscopy for tissue discrimination.

In a further aspect of the embodiment, the pedicle screw contains openings to the side that are in connection to the top portion of the pedicle screw. In this way fluids like biocompatible cement can be injected through the screw into the surrounding tissue. Such fluids may be cement that hardens upon injection or curable resin. The curing can be done for instance by heat, chemically or by light (such as UV hardening). Due to this curing of an injected fluid the fixation of the screw can be improved. During the curing phase the hardness of the curable resin can be interrogated with the color changing material on pressure at the fiber tip.

In a further modification, the sensing part can be integrated in any other part of the pedicle screw placement system such as the K-wire. As is known in the art, in certain procedures it may be needed to first place a K-wire in the bone, following which the pedicle screw to be implanted may be slided over this K-wire which can be removed after the screw has been placed.

In particular and in the context of an advantageous embodiment, the invention relates to pedicle screw system including a screw being of a biocompatible material and containing at least one optical waveguide, a biocompatible k-wire integrated with optical waveguide, wherein a distal end of the optical waveguide is positioned near the tip of the screw and a proximal end of the waveguide is connected to an optical console capable of sending and receiving light, pressure sensitive material that changes color upon application of pressure coated at least partly on the distal end of the waveguide, a console capable of sending light in the waveguide and able to receive the light that has interacted with the color changing material and with the tissue near the screw tip, a monitor connected to the console, wherein the console is capable of translating the received light (1) into tissue specific parameters and (2) into the amount of pressure exercised on the screw tip based on the color of the color changing material.

In a more preferred modification of the embodiment the pedicle screw has openings to allow fluids being injected through the screw. These fluids can for instance but not limited to be self-hardening cement or curable resins such as UV hardening resin.

In an even further preferred modification of the embodiment the pedicle screw system is equipped with impedance sensors for tissue discrimination.

In a further embodiment, the invention provides for a pedicle screw placement device including of a pedicle screw, a screwdriver, a stylet inside the pedicle screw allowing tissue sensing at the tip of the screw and an optical console capable of analyzing the optical signal and providing a feedback signal to the physician indicative for tissue in front of the screw.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single processor, device or other unit may fulfill the functions of several items recited in the claims. The mere fact that certain measures are recited in mutually different dependent claims does not indicate that a combination of these measures cannot be used to advantage.

Operations like determining, calculating, comparing and outputting (e.g. outputting a signal) can be implemented as program code means of a computer program and/or as dedicated hardware.

A computer program may be stored and/or distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A system comprising:
an implantable device comprising:
a k-wire configured to be placed into bone tissue, the k-wire integrated with an optical waveguide, and
a pedicle screw having an internal chamber configured to slide the pedicle screw over the k-wire and receive the optical waveguide in the internal chamber;
a light detector coupleable to an the k-wire, the light detector configured to receive light reflected by bone tissue at at least one of a tip of the k-wire and a tip of the screw and detect a spectrum of the reflected light; and
a processor coupleable to the light detector, the processor configured to receive the detected spectrum of light from the light detector and translate the detected spectrum into an indication related to the bone tissue.

2. The system according to claim 1, wherein a distal end of the optical waveguide is positioned at a distal end of the optical transmission device and a proximal end of the optical waveguide is connect to the light detector.

3. The system according to claim to claim 1, further comprising a screwing tool configured to couple to the pedicle screw for turning the pedicle screw.

4. The system according to claim 1, wherein the internal chamber has a notch configured to receive a fixating element, and the fixating element is configured to fixate the k-wire to the internal chamber in an axial direction, such that the implantable device has free rotational movement about the k-wire.

5. The system according to claim 1, further comprising:
a pressure sensitive portion situated at a distal end of the k-wire, the pressure sensitive portion forming part of an outer surface of the implantable device, the pressure sensitive portion i-s-configured to exhibit an optical response indicative of an amount of pressure applied to the pressure sensitive portion; and
a pressure sensor configured to determine a pressure applied to the pressure sensitive portion and output a signal indicative of the optical response,
wherein the light detector is further configured to detect the optical response.

6. The system according to claim 5, wherein the pressure sensitive portion includes one or more of piezochromic material and piezoluminescent material.

7. The system according to claim 1, further comprising a fluid dispenser coupleable to the implantable device and configured to dispense a liquid through the implantable device into the bone tissue.

8. The system according to claim 1, wherein the k-wire and the pedicle screw are made of biocompatible material.

9. An implantation device comprising:
a k-wire configured for placement into bone tissue, the k-wire integrated with an optical waveguide; and
a pedicle screw having a shaft configured to slide the pedicle screw over the k-wire and position a distal end of the optical waveguide at a tip of the pedicle screw,
wherein the optical waveguide is connectable, at a proximal end, to a processor configured to receive a spectrum of light reflected by bone tissue at at least one of the tip of the pedicle screw and a tip of the k-wire and translate the spectrum of the reflected light into an indication related to the bone tissue.

10. The device of claim 9, wherein the k-wire and the pedicle screw are made of biocompatible material.

11. The device of claim 9, further comprising a screwing tool configured to couple to the pedicle screw for turning the pedicle screw.

12. The device of claim 9, wherein the shaft has a notch configured to receive a fixating element, and the fixating element is configured to fixate the k-wire to the shaft in an axial direction, such that the implantation device has free rotational movement about the k-wire.

13. The device of claim 12, further comprising:
a fluid dispenser configured to dispense a liquid through the implantation device into the bone tissue.

14. The device of claim 9, wherein the optical waveguide is connectable to the processor via a light detector configured to receive the light reflected by the bone tissue and detect the spectrum of the reflected light.

15. The device of claim 14, further comprising:
a pressure sensitive portion situated at a distal end of the k-wire, the pressure sensitive portion forming part of an outer surface of the implantation device, the pressure sensitive portion configured to exhibit an optical response indicative of an amount of pressure applied to the pressure sensitive portion; and
a pressure sensor configured to determine a pressure applied to the pressure sensitive portion and output a signal indicative of the optical response,
wherein the light detector is further configured to detect the optical response.

16. The device according to claim 15, wherein the pressure sensitive portion includes at least one of piezochromic material and piezoluminescent material.

17. The system according to claim 1, wherein, to translate the detected spectrum into the indication, the processor is further configured to:
calculate a parameter indicative of a fat content in the bone tissue based on the detected spectrum of light,
compare the calculated parameter with a predetermined value, and
output the indication based on a result of the compare.

18. The system according to claim 17, wherein the indication is a warning indicating that the bone tissue reached by the implantable device is compact bone, if the result indicates that the calculated parameter is less than the predetermined value.

19. The system according to claim 17, wherein the indication specifies that the bone tissue reached by the implantable device is cancellous bone, if the result indicates that the calculated parameter is more than the predetermined value.

20. The system according to claim 17, wherein the processor is further configured to set the predetermined value based on a spectrum detected at a portion of tissue with a known bone tissue type.

* * * * *